US010169868B2

(12) United States Patent
Yoshida

(10) Patent No.: US 10,169,868 B2
(45) Date of Patent: Jan. 1, 2019

(54) IMAGE PROCESSING APPARATUS AND IMAGE PROCESSING METHOD

(71) Applicant: Toshiba Medical Systems Corporation, Otawara-shi (JP)

(72) Inventor: Masaki Yoshida, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 234 days.

(21) Appl. No.: 15/351,796

(22) Filed: Nov. 15, 2016

(65) Prior Publication Data

US 2017/0140529 A1 May 18, 2017

(30) Foreign Application Priority Data

Nov. 16, 2015 (JP) .................. 2015-224271

(51) Int. Cl.
*G06T 7/00* (2017.01)
*G06T 7/155* (2017.01)
*G06T 7/136* (2017.01)
*G06F 19/00* (2018.01)

(52) U.S. Cl.
CPC ............ *G06T 7/0012* (2013.01); *G06T 7/136* (2017.01); *G06T 7/155* (2017.01); *G06F 19/321* (2013.01); *G06T 2207/10081* (2013.01); *G06T 2207/10088* (2013.01); *G06T 2207/20101* (2013.01); *G06T 2207/30008* (2013.01); *G06T 2210/41* (2013.01)

(58) Field of Classification Search
CPC ....... G06T 7/0012; G06T 7/136; G06T 7/155; G06T 2207/10081; G06T 2207/10088; G06T 2207/20101; G06T 2207/30008; G06T 2210/41; G06F 19/321
See application file for complete search history.

(56) References Cited

U.S. PATENT DOCUMENTS

| | | | | |
|---|---|---|---|---|
| 4,893,346 A | * | 1/1990 | Bishop | .................... G06T 7/001 382/147 |
| 5,268,967 A | * | 12/1993 | Jang | ..................... G06T 7/0012 382/132 |
| 5,457,754 A | * | 10/1995 | Han | ...................... G06T 7/0012 382/128 |
| 5,615,243 A | * | 3/1997 | Chang | ................... G06T 7/0012 378/37 |

(Continued)

FOREIGN PATENT DOCUMENTS

| | | |
|---|---|---|
| JP | 2003-150966 | 5/2003 |
| JP | 2008-18016 | 1/2008 |
| JP | 2008-67992 | 3/2008 |

*Primary Examiner* — Manav Seth
(74) *Attorney, Agent, or Firm* — Oblon, McClelland, Maier & Neustadt, L.L.P.

(57) ABSTRACT

An image processing apparatus according to an embodiment includes processing circuitry. The processing circuitry sets a reference position in an area extracted by performing first processing on first image data. The processing circuitry sets a processing condition based on a pixel value at the reference position. The processing circuitry changes a threshold included in the processing condition in stages and performs second processing for extracting an area corresponding to the threshold on the first image data at each stage, thereby generating second image data including a result of the second processing at each stage.

10 Claims, 17 Drawing Sheets

(56) References Cited

U.S. PATENT DOCUMENTS

| | | | | |
|---|---|---|---|---|
| 5,680,471 A * | 10/1997 | Kanebako | G06T 7/0012 | 382/128 |
| 5,768,412 A * | 6/1998 | Mitsuyama | G06K 9/00127 | 382/133 |
| 5,999,639 A * | 12/1999 | Rogers | B25J 15/04 | 382/132 |
| 6,021,213 A * | 2/2000 | Helterbrand | G06T 7/11 | 382/128 |
| 6,091,841 A * | 7/2000 | Rogers | B25J 15/04 | 382/132 |
| 6,141,437 A * | 10/2000 | Xu | G06T 7/0012 | 128/922 |
| 6,246,784 B1 * | 6/2001 | Summers | G06K 9/00201 | 382/128 |
| 6,345,112 B1 * | 2/2002 | Summers | G06K 9/00201 | 382/128 |
| 6,556,696 B1 * | 4/2003 | Summers | G06K 9/00201 | 382/128 |
| 6,978,039 B2 * | 12/2005 | Cline | G06T 7/0012 | 128/922 |
| 7,054,485 B2 * | 5/2006 | Li | H04N 1/4092 | 382/171 |
| 7,149,564 B2 * | 12/2006 | Vining | A61B 5/1076 | 600/425 |
| 7,289,653 B2 * | 10/2007 | Zhang | G06T 7/11 | 382/131 |
| 7,330,589 B2 * | 2/2008 | Watanabe | G06T 7/11 | 382/171 |
| 7,333,648 B2 * | 2/2008 | Edic | G06T 7/0012 | 382/131 |
| 7,499,578 B2 * | 3/2009 | Reeves | G06T 3/0075 | 382/128 |
| 7,848,555 B2 * | 12/2010 | Zhang | G06T 7/0012 | 378/37 |
| 7,853,310 B2 * | 12/2010 | Vining | A61B 5/1076 | 600/425 |

* cited by examiner

FIG.2

| | | | | | | | | | | | | | | | 60 |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 |
| 0 | 1 | 1 | 1 | 1 | 1 | 0 | 0 | 0 | 0 | 2 | 2 | 2 | 0 | 0 | 0 |
| 0 | 1 | 0 | 0 | 0 | 1 | 0 | 0 | 0 | 0 | 2 | 3 | 2 | 0 | 0 | 0 |
| 0 | 1 | 0 | 3 | 0 | 1 | 0 | 0 | 0 | 0 | 2 | 2 | 2 | 0 | 0 | 0 |
| 0 | 1 | 0 | 0 | 0 | 1 | 0 | 0 | 0 | 0 | 0 | 0 | 0 | 0 | 0 | 0 |
| 0 | 1 | 1 | 1 | 1 | 1 | 0 | 0 | 0 | 0 | 0 | 0 | 0 | 0 | 0 | 0 |
| 0 | 0 | 0 | 1 | 1 | 1 | 1 | 1 | 1 | 1 | 1 | 1 | 1 | 1 | 0 | 0 |
| 0 | 0 | 0 | 1 | 2 | 2 | 2 | 2 | 2 | 1 | 1 | 1 | 1 | 1 | 0 | 0 |
| 0 | 0 | 0 | 1 | 2 | 1 | 1 | 1 | 2 | 1 | 1 | 1 | 1 | 1 | 0 | 0 |
| 0 | 0 | 0 | 1 | 2 | 1 | 3 | 1 | 2 | 1 | 1 | 1 | 1 | 1 | 0 | 0 |
| 0 | 0 | 0 | 1 | 2 | 1 | 1 | 1 | 2 | 1 | 1 | 1 | 1 | 1 | 0 | 0 |
| 0 | 0 | 0 | 1 | 2 | 2 | 2 | 2 | 2 | 1 | 1 | 1 | 1 | 1 | 0 | 0 |
| 0 | 0 | 0 | 1 | 1 | 2 | 2 | 2 | 2 | 1 | 1 | 1 | 1 | 1 | 0 | 0 |
| 0 | 0 | 0 | 1 | 1 | 2 | 2 | 2 | 2 | 2 | 2 | 2 | 2 | 1 | 0 | 0 |
| 0 | 0 | 0 | 1 | 1 | 2 | 3 | 3 | 3 | 3 | 3 | 3 | 2 | 1 | 0 | 0 |
| 0 | 0 | 0 | 1 | 1 | 2 | 3 | 4 | 4 | 5 | 4 | 4 | 2 | 1 | 0 | 0 |
| 0 | 0 | 0 | 1 | 1 | 2 | 3 | 3 | 3 | 3 | 3 | 3 | 2 | 1 | 0 | 0 |
| 0 | 0 | 0 | 1 | 1 | 2 | 2 | 2 | 2 | 2 | 2 | 2 | 2 | 1 | 0 | 0 |
| 0 | 0 | 0 | 1 | 1 | 1 | 1 | 1 | 1 | 1 | 1 | 1 | 1 | 1 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |

| | | | | | | | | | | | | | | | 60 |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 |
| 0 | 1 | 1 | 1 | 1 | 1 | 0 | 0 | 0 | 0 | 2 | 2 | 2 | 0 | 0 | 0 |
| 0 | 1 | 0 | 0 | 0 | 1 | 0 | 0 | 0 | 0 | 2 | 3 | 2 | 0 | 0 | 0 |
| 0 | 1 | 0 | 3 | 0 | 1 | 0 | 0 | 0 | 0 | 2 | 2 | 2 | 0 | 0 | 0 |
| 0 | 1 | 0 | 0 | 0 | 1 | 0 | 0 | 0 | 0 | 0 | 0 | 0 | 0 | 0 | 0 |
| 0 | 1 | 1 | 1 | 1 | 1 | 0 | 0 | 0 | 0 | 0 | 0 | 0 | 0 | 0 | 0 |
| 0 | 0 | 0 | 1 | 1 | 1 | 1 | 1 | 1 | 1 | 1 | 1 | 1 | 1 | 0 | 0 |
| 0 | 0 | 0 | 1 | 2 | 2 | 2 | 2 | 2 | 1 | 1 | 1 | 1 | 1 | 0 | 0 |
| 0 | 0 | 0 | 1 | 2 | 1 | 1 | 1 | 2 | 1 | 1 | 1 | 1 | 1 | 0 | 0 |
| 0 | 0 | 0 | 1 | 2 | 1 | 3 | 1 | 2 | 1 | 1 | 1 | 1 | 1 | 0 | 0 |
| 0 | 0 | 0 | 1 | 2 | 1 | 1 | 1 | 2 | 1 | 1 | 1 | 1 | 1 | 0 | 0 |
| 0 | 0 | 0 | 1 | 2 | 2 | 2 | 2 | 2 | 1 | 1 | 1 | 1 | 1 | 0 | 0 |
| 0 | 0 | 0 | 1 | 1 | 2 | 2 | 2 | 2 | 1 | 1 | 1 | 1 | 1 | 0 | 0 |
| 0 | 0 | 0 | 1 | 1 | 2 | 2 | 2 | 2 | 2 | 2 | 2 | 2 | 1 | 0 | 0 |
| 0 | 0 | 0 | 1 | 1 | 2 | 3 | 3 | 3 | 3 | 3 | 3 | 2 | 1 | 0 | 0 |
| 0 | 0 | 0 | 1 | 1 | 2 | 3 | 4 | 4 | 5 | 4 | 4 | 2 | 1 | 0 | 0 |
| 0 | 0 | 0 | 1 | 1 | 2 | 3 | 3 | 3 | 3 | 3 | 3 | 2 | 1 | 0 | 0 |
| 0 | 0 | 0 | 1 | 1 | 2 | 2 | 2 | 2 | 2 | 2 | 2 | 2 | 1 | 0 | 0 |
| 0 | 0 | 0 | 1 | 1 | 1 | 1 | 1 | 1 | 1 | 1 | 1 | 1 | 1 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |

61   62

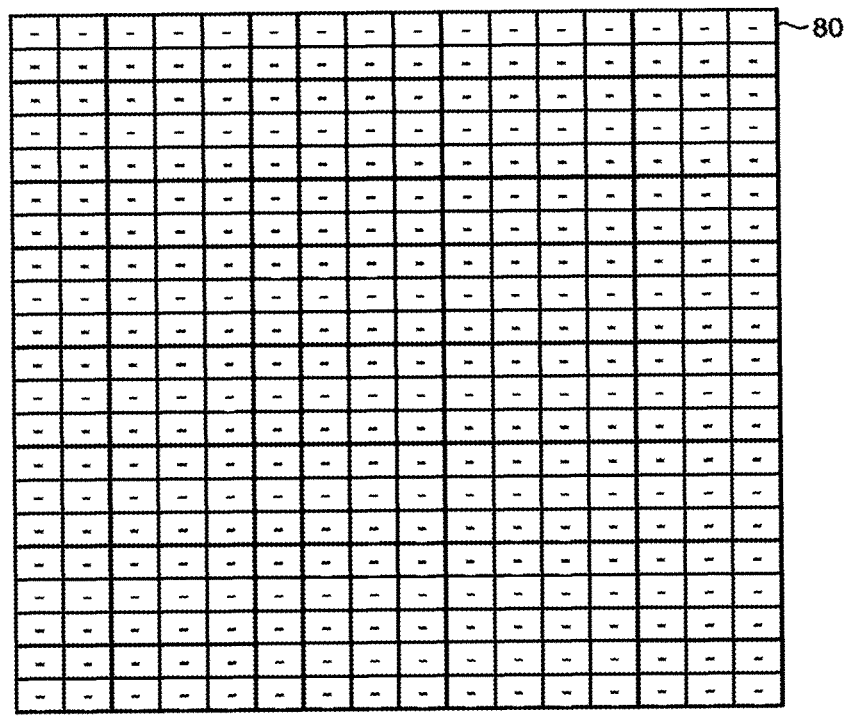

FIG.7A

| 0 | 0 | 0 | 0 | 0 | 0 | 0 | 0 | 0 | 0 | 0 | 0 | 0 | 0 | 0 | 0 |
|---|---|---|---|---|---|---|---|---|---|---|---|---|---|---|---|
| 0 | 1 | 1 | 1 | 1 | 1 | 0 | 0 | 0 | 0 | 2 | 2 | 2 | 0 | 0 | 0 |
| 0 | 1 | 0 | 0 | 0 | 1 | 0 | 0 | 0 | 0 | 2 | 3 | 2 | 0 | 0 | 0 |
| 0 | 1 | 0 | 3 | 0 | 1 | 0 | 0 | 0 | 0 | 2 | 2 | 2 | 0 | 0 | 0 |
| 0 | 1 | 0 | 0 | 0 | 1 | 0 | 0 | 0 | 0 | 0 | 0 | 0 | 0 | 0 | 0 |
| 0 | 1 | 1 | 1 | 1 | 1 | 0 | 0 | 0 | 0 | 0 | 0 | 0 | 0 | 0 | 0 |
| 0 | 0 | 0 | 1 | 1 | 1 | 1 | 1 | 1 | 1 | 1 | 1 | 1 | 1 | 0 | 0 |
| 0 | 0 | 0 | 1 | 2 | 2 | 2 | 2 | 2 | 1 | 1 | 1 | 1 | 1 | 0 | 0 |
| 0 | 0 | 0 | 1 | 2 | 1 | 1 | 1 | 2 | 1 | 1 | 1 | 1 | 1 | 0 | 0 |
| 0 | 0 | 0 | 1 | 2 | 1 | 3 | 1 | 2 | 1 | 1 | 1 | 1 | 1 | 0 | 0 |
| 0 | 0 | 0 | 1 | 2 | 1 | 1 | 1 | 2 | 1 | 1 | 1 | 1 | 1 | 0 | 0 |
| 0 | 0 | 0 | 1 | 2 | 2 | 2 | 2 | 2 | 1 | 1 | 1 | 1 | 1 | 0 | 0 |
| 0 | 0 | 0 | 1 | 1 | 2 | 2 | 2 | 2 | 1 | 1 | 1 | 1 | 1 | 0 | 0 |
| 0 | 0 | 0 | 1 | 1 | 2 | 2 | 2 | 2 | 2 | 2 | 2 | 2 | 1 | 0 | 0 |
| 0 | 0 | 0 | 1 | 1 | 2 | 3 | 3 | 3 | 3 | 3 | 3 | 2 | 1 | 0 | 0 |
| 0 | 0 | 0 | 1 | 1 | 2 | 3 | 4 | 4 | 5 | 4 | 4 | 2 | 1 | 0 | 0 |
| 0 | 0 | 0 | 1 | 1 | 2 | 3 | 3 | 3 | 3 | 3 | 3 | 2 | 1 | 0 | 0 |
| 0 | 0 | 0 | 1 | 1 | 2 | 2 | 2 | 2 | 2 | 2 | 2 | 2 | 1 | 0 | 0 |
| 0 | 0 | 0 | 1 | 1 | 1 | 1 | 1 | 1 | 1 | 1 | 1 | 1 | 1 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |

FIG.7B

A grid of the same dimensions filled with "-" except for one highlighted cell containing "5" (labeled 81).

FIG.8A

| 0 | 0 | 0 | 0 | 0 | 0 | 0 | 0 | 0 | 0 | 0 | 0 | 0 | 0 | 0 | 0 |
|---|---|---|---|---|---|---|---|---|---|---|---|---|---|---|---|
| 0 | 1 | 1 | 1 | 1 | 1 | 0 | 0 | 0 | 2 | 2 | 2 | 0 | 0 | 0 |   |
| 0 | 1 | 0 | 0 | 0 | 1 | 0 | 0 | 0 | 2 | 3 | 2 | 0 | 0 | 0 |   |
| 0 | 1 | 0 | 3 | 0 | 1 | 0 | 0 | 0 | 2 | 2 | 2 | 0 | 0 | 0 |   |
| 0 | 1 | 0 | 0 | 0 | 1 | 0 | 0 | 0 | 0 | 0 | 0 | 0 | 0 | 0 |   |
| 0 | 1 | 1 | 1 | 1 | 1 | 0 | 0 | 0 | 0 | 0 | 0 | 0 | 0 | 0 |   |
| 0 | 0 | 0 | 1 | 1 | 1 | 1 | 1 | 1 | 1 | 1 | 1 | 1 | 0 | 0 |   |
| 0 | 0 | 0 | 1 | 2 | 2 | 2 | 2 | 1 | 1 | 1 | 1 | 1 | 0 | 0 |   |
| 0 | 0 | 0 | 1 | 2 | 1 | 1 | 1 | 2 | 1 | 1 | 1 | 1 | 0 | 0 |   |
| 0 | 0 | 0 | 1 | 2 | 1 | 3 | 1 | 2 | 1 | 1 | 1 | 1 | 0 | 0 |   |
| 0 | 0 | 0 | 1 | 2 | 1 | 1 | 1 | 2 | 1 | 1 | 1 | 1 | 0 | 0 |   |
| 0 | 0 | 0 | 1 | 2 | 2 | 2 | 2 | 2 | 1 | 1 | 1 | 1 | 0 | 0 |   |
| 0 | 0 | 0 | 1 | 1 | 2 | 2 | 2 | 2 | 1 | 1 | 1 | 1 | 0 | 0 |   |
| 0 | 0 | 0 | 1 | 1 | 2 | 2 | 2 | 2 | 2 | 2 | 2 | 1 | 0 | 0 |   |
| 0 | 0 | 0 | 1 | 1 | 2 | 3 | 3 | 3 | 3 | 3 | 2 | 1 | 0 | 0 |   |
| 0 | 0 | 0 | 1 | 1 | 2 | 3 | 4 | 4 | 5 | 4 | 4 | 2 | 1 | 0 | 0 |
| 0 | 0 | 0 | 1 | 1 | 2 | 3 | 3 | 3 | 3 | 3 | 2 | 1 | 0 | 0 |   |
| 0 | 0 | 0 | 1 | 1 | 2 | 2 | 2 | 2 | 2 | 2 | 2 | 1 | 0 | 0 |   |
| 0 | 0 | 0 | 1 | 1 | 1 | 1 | 1 | 1 | 1 | 1 | 1 | 1 | 0 | 0 |   |
| 0 | 0 | 0 | 0 | 0 | 0 | 0 | 0 | 0 | 0 | 0 | 0 | 0 | 0 | 0 |   |
| 0 | 0 | 0 | 0 | 0 | 0 | 0 | 0 | 0 | 0 | 0 | 0 | 0 | 0 | 0 |   |

~60

63 63 62 63 63

FIG.8B (Grid filled with "-" except row showing: 4 4 5 4 4)

| | | | 64a | | | 64b | | | | | | | | | | |
|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | ~60 |
| 0 | 1 | 1 | 1 | 1 | 1 | 0 | 0 | 0 | 0 | 2 | 2 | 2 | 0 | 0 | 0 | |
| 0 | 1 | 0 | 0 | 0 | 1 | 0 | 0 | 0 | 0 | 2 | 3 | 2 | 0 | 0 | 0 | |
| 0 | 1 | 0 | 3 | 0 | 1 | 0 | 0 | 0 | 0 | 2 | 2 | 2 | 0 | 0 | 0 | |
| 0 | 1 | 0 | 0 | 0 | 1 | 0 | 0 | 0 | 0 | 0 | 0 | 0 | 0 | 0 | 0 | |
| 0 | 1 | 1 | 1 | 1 | 1 | 0 | 0 | 0 | 0 | 0 | 0 | 0 | 0 | 0 | 0 | |
| 0 | 0 | 0 | 1 | 1 | 1 | 1 | 1 | 1 | 1 | 1 | 1 | 1 | 1 | 0 | 0 | |
| 0 | 0 | 0 | 1 | 2 | 2 | 2 | 2 | 2 | 1 | 1 | 1 | 1 | 1 | 0 | 0 | |
| 0 | 0 | 0 | 1 | 2 | 1 | 1 | 1 | 2 | 1 | 1 | 1 | 1 | 1 | 0 | 0 | |
| 0 | 0 | 0 | 1 | 2 | 1 | 3 | 1 | 2 | 1 | 1 | 1 | 1 | 1 | 0 | 0 | |
| 0 | 0 | 0 | 1 | 2 | 1 | 1 | 1 | 2 | 1 | 1 | 1 | 1 | 1 | 0 | 0 | |
| 0 | 0 | 0 | 1 | 2 | 2 | 2 | 2 | 2 | 1 | 1 | 1 | 1 | 1 | 0 | 0 | |
| 0 | 0 | 0 | 1 | 1 | 2 | 2 | 2 | 2 | 1 | 1 | 1 | 1 | 1 | 0 | 0 | |
| 0 | 0 | 0 | 1 | 1 | 2 | 2 | 2 | 2 | 2 | 2 | 2 | 2 | 1 | 0 | 0 | |
| 0 | 0 | 0 | 1 | 1 | 2 | 3 | 3 | 3 | 3 | 3 | 3 | 2 | 1 | 0 | 0 | |
| 0 | 0 | 0 | 1 | 1 | 2 | 3 | 4 | 4 | 5 | 4 | 4 | 2 | 1 | 0 | 0 | |
| 0 | 0 | 0 | 1 | 1 | 2 | 3 | 3 | 3 | 3 | 3 | 3 | 2 | 1 | 0 | 0 | |
| 0 | 0 | 0 | 1 | 1 | 2 | 2 | 2 | 2 | 2 | 2 | 2 | 2 | 1 | 0 | 0 | |
| 0 | 0 | 0 | 1 | 1 | 1 | 1 | 1 | 1 | 1 | 1 | 1 | 1 | 1 | 0 | 0 | |
| 0 | 0 | 0 | 0 | 0 | 0 | 0 | 0 | 0 | 0 | 0 | 0 | 0 | 0 | 0 | 0 | |
| 0 | 0 | 0 | 0 | 0 | 0 | 0 | 0 | 0 | 0 | 0 | 0 | 0 | 0 | 0 | 0 | |

| | | | | | | | | | | | | | | | | |
|---|---|---|---|---|---|---|---|---|---|---|---|---|---|---|---|---|
| - | - | - | - | - | - | - | - | - | - | - | - | - | - | - | - | ~80 |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | 3 | 3 | 3 | 3 | 3 | 3 | - | - | - | - | |
| - | - | - | - | - | - | 3 | 4 | 4 | 5 | 4 | 4 | - | - | - | - | |
| - | - | - | - | - | - | 3 | 3 | 3 | 3 | 3 | 3 | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |
| - | - | - | - | - | - | - | - | - | - | - | - | - | - | - | - | |

| | | | | | | | | | | | | | | |
|---|---|---|---|---|---|---|---|---|---|---|---|---|---|---|
|0|0|0|0|0|0|0|0|0|0|0|0|0|0|0|
|0|1|1|1|1|0|0|0|0|2|2|2|0|0|0|
|0|1|0|0|1|0|0|0|0|2|3|2|0|0|0|
|0|1|0|3|0|1|0|0|0|2|2|2|0|0|0|
|0|1|0|0|0|1|0|0|0|0|0|0|0|0|0|
|0|1|1|1|1|0|0|0|0|0|0|0|0|0|0|
|0|0|0|1|1|1|1|1|1|1|1|1|1|0|0|
|0|0|0|1|2|2|2|2|2|1|1|1|1|0|0|
|0|0|0|1|2|1|1|1|2|1|1|1|1|0|0|
|0|0|0|1|2|1|3|1|2|1|1|1|1|0|0|
|0|0|0|1|2|1|1|1|2|1|1|1|1|0|0|
|0|0|0|1|2|2|2|2|2|1|1|1|1|0|0|
|0|0|0|1|1|2|2|2|2|1|1|1|1|0|0|
|0|0|0|1|1|2|2|2|2|2|2|2|1|0|0|
|0|0|0|1|1|2|3|3|3|3|3|2|1|0|0|
|0|0|0|1|1|2|3|4|4|5|4|4|2|1|0|
|0|0|0|1|1|2|3|3|3|3|3|3|2|1|0|
|0|0|0|1|1|2|2|2|2|2|2|2|2|1|0|
|0|0|0|1|1|1|1|1|1|1|1|1|1|1|0|
|0|0|0|0|0|0|0|0|0|0|0|0|0|0|0|
|0|0|0|0|0|0|0|0|0|0|0|0|0|0|0|

| | | | | | | | | | | | | | | |
|---|---|---|---|---|---|---|---|---|---|---|---|---|---|---|
|-|-|-|-|-|-|-|-|-|-|-|-|-|-|-|
|-|-|-|-|-|-|-|-|-|-|-|-|-|-|-|
|-|-|-|-|-|-|-|-|-|-|-|-|-|-|-|
|-|-|-|-|-|-|-|-|-|-|-|-|-|-|-|
|-|-|-|-|-|-|-|-|-|-|-|-|-|-|-|
|-|-|-|-|-|-|-|-|-|-|-|-|-|-|-|
|-|-|-|-|-|-|-|-|-|-|-|-|-|-|-|
|-|-|-|-|2|2|2|2|2|-|-|-|-|-|-|
|-|-|-|-|2|-|-|-|2|-|-|-|-|-|-|
|-|-|-|-|2|-|-|-|2|-|-|-|-|-|-|
|-|-|-|-|2|-|-|-|2|-|-|-|-|-|-|
|-|-|-|-|2|2|2|2|2|-|-|-|-|-|-|
|-|-|-|-|-|2|2|2|2|-|-|-|-|-|-|
|-|-|-|-|-|2|2|2|2|2|2|2|-|-|-|
|-|-|-|-|-|2|3|3|3|3|3|2|-|-|-|
|-|-|-|-|-|2|3|4|4|5|4|4|2|-|-|
|-|-|-|-|-|2|3|3|3|3|3|3|2|-|-|
|-|-|-|-|-|2|2|2|2|2|2|2|2|-|-|
|-|-|-|-|-|-|-|-|-|-|-|-|-|-|-|
|-|-|-|-|-|-|-|-|-|-|-|-|-|-|-|
|-|-|-|-|-|-|-|-|-|-|-|-|-|-|-|

| | | | | | | | | | | | | | | | | |
|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | ~60 |
| 0 | 1 | 1 | 1 | 1 | 1 | 0 | 0 | 0 | 0 | 2 | 2 | 2 | 0 | 0 | 0 | |
| 0 | 1 | 0 | 0 | 0 | 1 | 0 | 0 | 0 | 0 | 2 | 3 | 2 | 0 | 0 | 0 | |
| 0 | 1 | 0 | 3 | 0 | 1 | 0 | 0 | 0 | 0 | 2 | 2 | 2 | 0 | 0 | 0 | |
| 0 | 1 | 0 | 0 | 0 | 1 | 0 | 0 | 0 | 0 | 0 | 0 | 0 | 0 | 0 | 0 | |
| 0 | 1 | 1 | 1 | 1 | 1 | 0 | 0 | 0 | 0 | 0 | 0 | 0 | 0 | 0 | 0 | |
| 0 | 0 | 0 | 1 | 1 | 1 | 1 | 1 | 1 | 1 | 1 | 1 | 1 | 1 | 0 | 0 | |
| 0 | 0 | 0 | 1 | 2 | 2 | 2 | 2 | 1 | 1 | 1 | 1 | 1 | 1 | 0 | 0 | |
| 0 | 0 | 0 | 1 | 2 | 1 | 1 | 2 | 1 | 1 | 1 | 1 | 1 | 1 | 0 | 0 | |
| 0 | 0 | 0 | 1 | 2 | 1 | 3 | 1 | 2 | 1 | 1 | 1 | 1 | 1 | 0 | 0 | |
| 0 | 0 | 0 | 1 | 2 | 1 | 1 | 1 | 2 | 1 | 1 | 1 | 1 | 1 | 0 | 0 | |
| 0 | 0 | 0 | 1 | 2 | 2 | 2 | 2 | 2 | 1 | 1 | 1 | 1 | 1 | 0 | 0 | |
| 0 | 0 | 0 | 1 | 1 | 2 | 2 | 2 | 2 | 1 | 1 | 1 | 1 | 1 | 0 | 0 | |
| 0 | 0 | 0 | 1 | 1 | 2 | 2 | 2 | 2 | 2 | 2 | 2 | 1 | 0 | 0 | 0 | |
| 0 | 0 | 0 | 1 | 1 | 2 | 3 | 3 | 3 | 3 | 3 | 2 | 1 | 0 | 0 | 0 | |
| 0 | 0 | 0 | 1 | 1 | 2 | 3 | 4 | 4 | 5 | 4 | 4 | 2 | 1 | 0 | 0 | |
| 0 | 0 | 0 | 1 | 1 | 2 | 3 | 3 | 3 | 3 | 3 | 3 | 2 | 1 | 0 | 0 | |
| 0 | 0 | 0 | 1 | 1 | 2 | 2 | 2 | 2 | 2 | 2 | 2 | 2 | 1 | 0 | 0 | |
| 0 | 0 | 0 | 1 | 1 | 1 | 1 | 1 | 1 | 1 | 1 | 1 | 1 | 0 | 0 | 0 | |
| 0 | 0 | 0 | 0 | 0 | 0 | 0 | 0 | 0 | 0 | 0 | 0 | 0 | 0 | 0 | 0 | |
| 0 | 0 | 0 | 0 | 0 | 0 | 0 | 0 | 0 | 0 | 0 | 0 | 0 | 0 | 0 | 0 | |

67  66 65 64  63 62

FIG.12B (referenced labels: 86, 85, 84, 83, 82, 81; region marker ~80)

IMAGE PROCESSING APPARATUS AND IMAGE PROCESSING METHOD

CROSS-REFERENCE TO RELATED APPLICATIONS

This application is based upon and claims the benefit of priority from Japanese Patent Application No. 2015-224271, filed on Nov. 16, 2015; the entire contents of which are incorporated herein by reference.

FIELD

Embodiments described herein relate generally to an image processing apparatus and an image processing method.

BACKGROUND

There have been developed image processing apparatuses that perform various types of image processing on an image obtained by medical image diagnosis apparatuses, such as X-ray computed tomography (CT) apparatuses and magnetic resonance imaging (MRI) apparatuses.

Such an image processing apparatus, for example, receives display conditions, such as a window width and a window level, for displaying an area including a specific region (e.g., a heart and a lung) from a user, such as a doctor who interprets radiograms. The image processing apparatus displays an image on a display under the received display conditions. The image processing apparatus thus displays the area including the specific region. The user gives, to the image processing apparatus, an instruction to perform segmentation for extracting only the specific region from the area displayed under the display conditions so as to observe only the specific region. When receiving the instruction, the image processing apparatus performs segmentation to extract the specific region from the displayed area and displays the extracted specific region on the display.

BRIEF DESCRIPTION OF THE DRAWINGS

FIG. 2 is a diagram of an example of an image indicated by image data acquired by a setting function;

FIG. 4 is a diagram for explaining an example of a method for setting a position of a seed point;

FIG. 5 is a diagram of an example of a segmentation result;

FIG. 6A is a diagram of an example of an initial state of a corrected image;

FIG. 6B is a diagram of an example of a result of segmentation performed under a segmentation condition C(6);

FIG. 7A is a diagram of an example of an area D(S, C(5));

FIG. 7B is a diagram of an example of the corrected image in which the luminance of a pixel is updated;

FIG. 8A is a diagram of an example of an area D(S, C(4));

FIG. 9A is a diagram of an example of the corrected image in which the luminance of pixels is updated;

FIG. 9A is a diagram of an example of an area D(S, C(3));

FIG. 9B is a diagram of an example of the corrected image in which the luminance of pixels is updated;

FIG. 10A is a diagram of an example of an area D(S, C(2));

FIG. 10B is a diagram of an example of the corrected image in which the luminance of pixels is updated;

FIG. 11A is a diagram of an example of an area D(S, C(1));

FIG. 11B is a diagram of an example of the corrected image in which the luminance of pixels is updated;

FIG. 12A is a diagram of an example of an area D(S, C(0));

FIG. 12B is a diagram of an example of the corrected image in which the luminance of pixels is updated;

DETAILED DESCRIPTION

An image processing apparatus according to an embodiment includes processing circuitry. The processing circuitry sets a reference position in an area extracted by performing first processing on first image data. The processing circuitry sets a processing condition based on a pixel value at the reference position. The processing circuitry changes a threshold included in the processing condition in stages and performs second processing for extracting an area corresponding to the threshold on the first image data at each stage, thereby generating second image data including a result of the second processing at each stage.

Exemplary embodiments of an image processing apparatus and an image processing program are described below in greater detail with reference to the accompanying drawings.

First Embodiment

Figure 1:
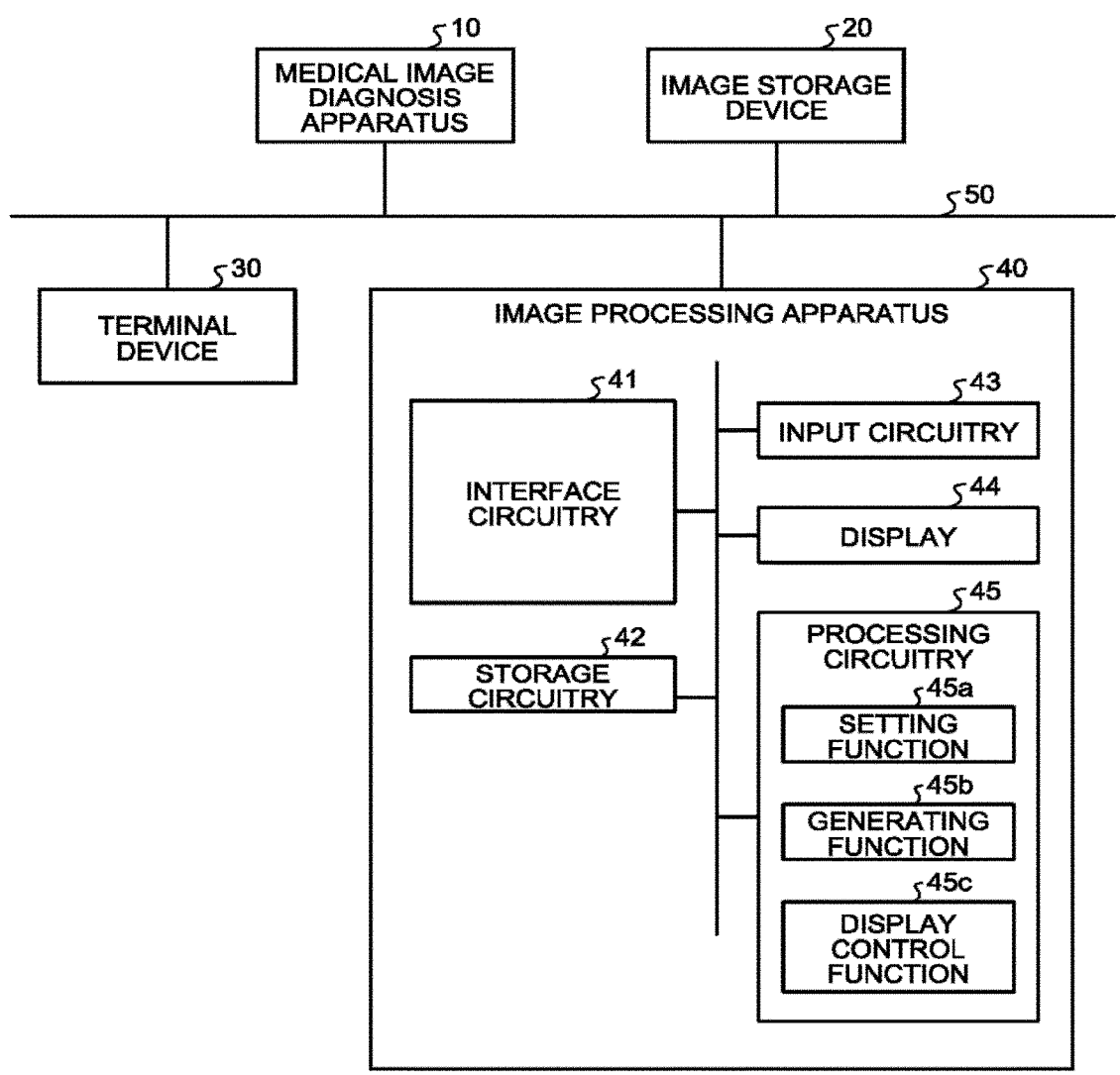
FIG. 1 is a diagram of an exemplary configuration of an image processing system including an image processing apparatus according to a first embodiment.

A configuration of an image processing system including an image processing apparatus according to a first embodiment will be described first. After a user adjusts display conditions, such as a window width and a window level, the image processing system according to the first embodiment performs segmentation on an image displayed under the adjusted display conditions. FIG. 1 is a diagram of an exemplary configuration of the image processing system including the image processing apparatus according to the first embodiment. The image processing system illustrated in the example in FIG. 1 includes a medical image diagnosis apparatus 10, an image storage device 20, a terminal device 30, and an image processing apparatus 40. The medical image diagnosis apparatus 10, the image storage device 20, the terminal device 30, and the image processing apparatus 40 can directly or indirectly communicate with one another via an in-hospital local area network (LAN) 50 installer in a hospital, for example. In a case where a picture archiving and communication system (PACS) is introduced, for example, the apparatuses and devices 10 to 40 mutually transmit and receive an image and other data according to the digital imaging and communications in medicine (DICOM) standard.

Examples of the medical image diagnosis apparatus 10 include various types of medical image diagnosis apparatuses, such as an MRI apparatus and an X-ray CT apparatus. The medical image diagnosis apparatus 10 transmits, to the image storage device 20 and the terminal device 30, image data indicating an image, such as a CT image and an MR image, resulting from radiography performed on a subject. In other words, the medical image diagnosis apparatus 10 transmits, to the image storage device 20 and the terminal device 30, image data indicating an image obtained by radiography performed on the subject.

The image storage device 20 is a database that ores therein image data transmitted from the medical image diagnosis apparatus 10 and the image processing apparatus 40. The image storage device 20 is a server having semiconductor memory device, such as a random access memory (RAM) and a flash memory, a hard disk, or an optical disc, for example.

The terminal device 30 is used to view a medical image by doctors, nurses, radiologists, or other staff members who work in a hospital. When receiving image data transmitted from the medical image diagnosis apparatus 10 and the image processing apparatus 40, the terminal device 30 displays an image indicated by the received image data. The terminal device 30 is a personal computer (PC), a tablet PC, a personal digital assistant (PDA), or a mobile phone, for example, operated by doctors, nurses, radiologists, or other staff members who work in a hospital.

The image processing apparatus 40 is a workstation. The image processing apparatus 40 acquires image data stored in the image storage device 20 and performs various types of image processing on an image indicated by the acquired image data. The image processing apparatus 40 transmits image data indicating the image subjected to the image processing to the image storage device 20 and the terminal device 30.

The image processing apparatus 40 includes interface circuitry 41, storage circuitry 42, input circuitry 43, a display 44, and processing circuitry 45.

The interface circuitry 41 is an interface that establishes communications between the image processing apparatus 40 and the medical image diagnosis apparatus 10, the image storage device 20, and the terminal device 30. When receiving image data acquired from the image storage device 20, for example, the interface circuitry 41 transmits the received image data to the processing circuitry 45. The interface circuitry 41 is a network interface card (NIC), for example.

The storage circuitry 42 stores therein image data and a corrected image generated by a generating function 45b, which will be described later, for example. The storage circuitry 42 stores therein various types of computer programs. The storage circuitry 42 stores therein an image processing program, for example. The storage circuitry 42 is a semiconductor memory device, such as a random access memory and a flash memory, a hard disk, or an optical disc, for example.

The input circuitry 43 receives various types instructions and input of information from an operator. The input circuitry 43 is a trackball, a switch button, a mouse, and a keyboard, for example. The input circuitry 43 is connected to the processing circuitry 45. The input circuitry 43 converts an input operation received from the operator into electrical signals and outputs them to the processing circuitry 45.

The display 44 displays various types of graphical user interfaces (GUI) and a corrected image generated by the generating function 45b, for example, under the control of the processing circuitry 45.

The processing circuitry 45 collectively controls the image processing apparatus 40. The processing circuitry 45 is a processor. The processing circuitry 45 includes a setting function 45a, the generating function 45b, and a display control function 45c. Functions performed by the setting function 45a, the generating function 45b, and the display control function 45c will be described later.

The functions of the setting function 45a, the generating function 45b, and the display control function 45c serving as components of the processing circuitry 45, for example, are stored in the storage circuitry 42 in the form of computer-executable programs. The processing circuitry 45 reads the computer programs from the storage circuitry 42 and executes the read computer programs, thereby performing the functions. In other words, when reading the computer programs, the processing circuitry 45 has the functions in the processing circuitry 45 illustrated in FIG. 1.

The term "processor" in the description above means a central processing unit (CPU), a graphics processing unit (GPU), or a circuitry, such as an application specific integrated circuit (ASIC) and a programmable logic device (e.g., a simple programmable logic device (SPLIT), a complex programmable logic device (CPLD), and a field programmable gate array (FPGA)). The computer programs may be directly embedded in a circuitry of the processor instead of being stored in the storage circuitry 42. In this case, the processor reads the computer programs embedded in the circuitry, thereby performing the functions.

The image processing apparatus may possibly perform the processing described below. The image processing apparatus, for example, receives display conditions, such as a window width and a window level, for displaying an area including a specific region (e.g., a heart and a lung) from a user, such as a doctor who interprets radiograms. The image processing apparatus displays an image on the display under the received display conditions. When receiving, from the user, the position of a seed point and an instruction to perform segmentation using a region growing method of sequentially repeating extraction of a pixel that is connected to the seed point and that satisfies a segmentation condition (that is, a pixel capable of being observed by the user), the image processing apparatus performs segmentation in response to the instruction. The segmentation condition is as follows: the luminance of the pixel is higher than the lower limit of the window determined based on the window level and the window width. The lower limit of the window determined based on the window level and the window width corresponds to a "threshold", which will be described later with reference to FIG. 3. In other words, the image processing apparatus sequentially repeats extraction of a pixel that is connected to the seed point and the luminance of which is higher than the lower limit of the window, thereby extracting pixels constituting a specific region. The image processing apparatus displays the specific region on the display. The image processing apparatus thus extracts the specific region from the displayed area, that is, the area capable of being observed by the user and displays the extracted specific region.

If the display conditions, such as the window width and the window level, are changed by the user while the extracted specific region is being displayed, the lower limit of the window is also changed. The image processing apparatus performs segmentation again. In other words, the image processing apparatus sequentially repeats, using the already received seed point, extraction of a pixel that is connected to the seed point and that satisfies the changed segmentation condition that the luminance of the pixel is higher than the changed lower limit of the window. As a result, the pixels constituting the specific region are extracted. The image processing apparatus displays the specific region extracted by the reperformed segmentation on the display. Every time the user changes the display conditions, the image processing apparatus performs segmentation under the segmentation condition based on the changed display conditions and displays the specific region extracted by the segmentation on the display.

If segmentation is performed every time the display conditions are changed, however, it takes time from when the display conditions are changed to when the pixels extracted by the segmentation are displayed on the display. Taking time decreases the usability.

The image processing apparatus may possibly perform the processing described below. The image processing apparatus, for example, performs segmentation under the segmentation condition based on all the conceivable display conditions. The image processing apparatus stores pixels extracted under all the display conditions in the storage circuitry in a manner associated with the respective display conditions. When the user changes the display conditions, the image processing apparatus refers to the storage contents in the storage circuitry. The image processing apparatus thus identifies pixels corresponding to the changed display conditions and displays the identified pixels on the display.

In this case, however, the pixels extracted under all the display conditions are stored in the storage circuitry in a manner associated with the respective display conditions. This mechanism reduces the free space in the storage circuitry.

The image processing apparatus 40 according to the present embodiment can quickly display a segmentation result using one corrected image that requires less storage capacity even when the display conditions are changed as described below.

The image processing apparatus 40 according to the present embodiment generates one corrected image, which will be described later, and displays the generated corrected image on the display 44 and/or the terminal device 30.

The following describes corrected image generation for generating one corrected image.

The setting function 45a acquires image data from the image storage device 20. FIG. 2 is a diagram of an example of an image indicated by image data acquired by the setting function 45a. FIG. 2 illustrates an image 60 composed of 336 (21×16) pixels, for example. The numerical values in the respective pixels indicate the luminance (pixel values) of the pixels. While the luminance of the pixels takes 0 to 5 in the example in FIG. 2, the range of the luminance of an image indicated by image data acquired by the setting function 45a according to the present embodiment is not limited thereto. In a case where the image indicated by the acquired image data is a CT image, for example, the range of the luminance may correspond to a range of the Hounsfield unit (HU) of −1000 to 1000. The setting function 45a is an example of a setting unit. The image indicated by image data acquired by the setting function 45a is an example of a first image.

The image data acquired by the setting function 45a is an example of first image data. The image data acquired by the setting function 45a may be three-dimensional data (volume data) or two-dimensional data.

The setting function 45a displays the image 60 on the display 44 and/or the terminal device 30 based on the window width and the window level set in advance. After the user, such as a doctor who interprets radiograms, checks the image 60 displayed on the display 44 and/or the terminal device 30, the user may operate the input circuitry 43 to change the window width and the window level.

Figure 3:
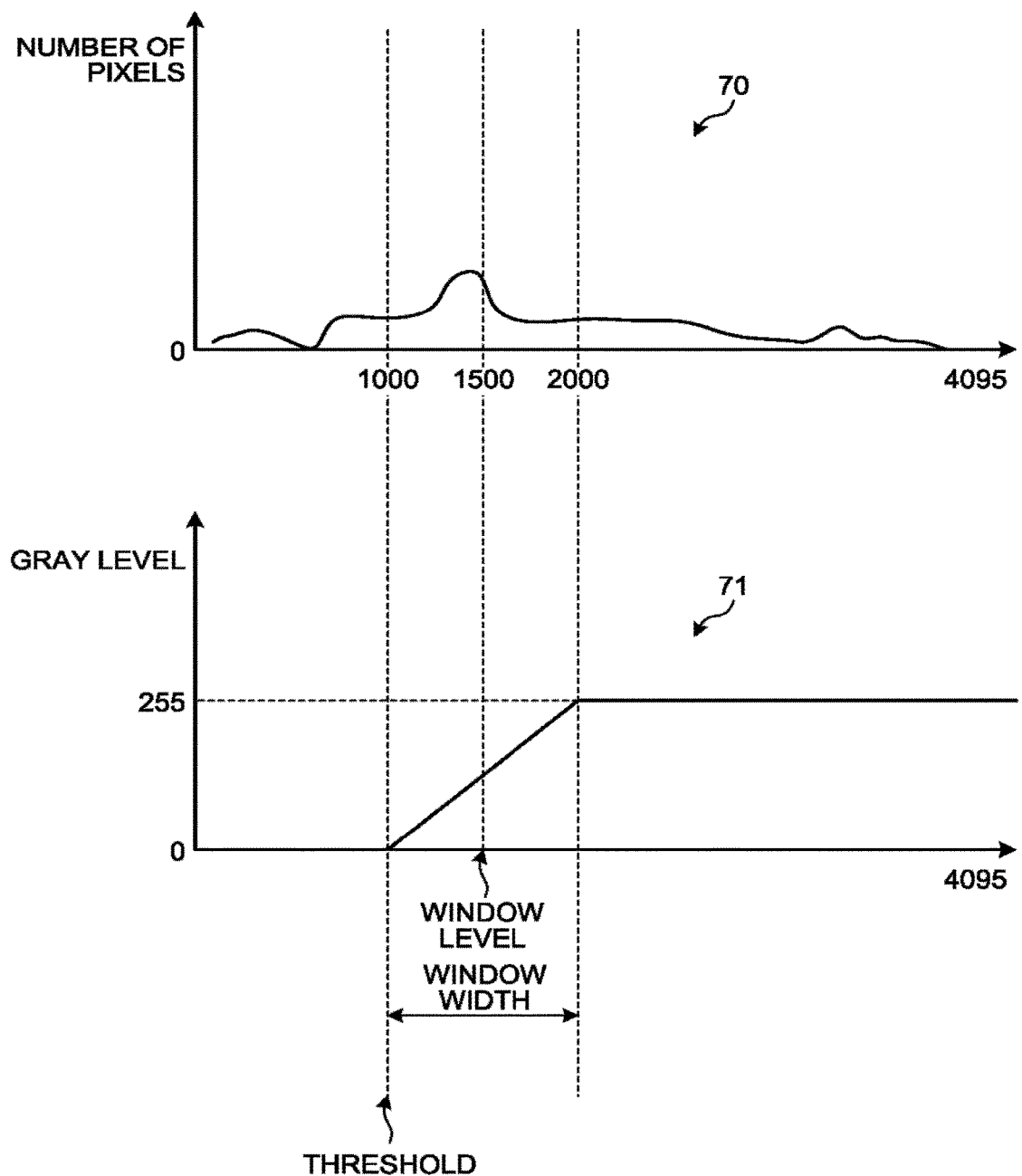
FIG. 3 is a diagram for explaining an example of a window width and a window level.

The following describes the window width and the window level. FIG. 3 is a diagram for explaining an example of the window width and the window level. In a graph 70 in the example illustrated in FIG. 3, the horizontal axis indicates the luminance of pixels constituting an image indicated by image data acquired from the image storage device 20 by the setting function 45a, and the vertical axis indicates the number of pixels. Let us assume a case where the user sets the window width to "1000" and the window level to "1500" in the example illustrated in FIG. 3. In this case, as indicated by a graph 71, pixels having luminance of 2000 or higher have a gray level of "255", whereas pixels having luminance of 1000 or lower have a gray level of "0". When S is the luminance, a gray level G of pixels having luminance of higher than 1000 and lower than 2000 is expressed by Expression (1):

$$G = (255/1000)S - 255 \tag{1}$$

The pixels are displayed on the display 44 and/or the terminal device 30 based on the gray level. In the example illustrated in FIG. 3, pixels having luminance of higher than 1000 are pixels displayed on the display 44 and/or the terminal device 30, that is, pixels capable of being observed by the user because they have a gray level of higher than 0. Because the present embodiment performs segmentation on an area capable of being observed by the user, it uses the lower limit of the window ("1000" in the example illustrated in FIG. 3) as a threshold, which will be described later, in the segmentation condition.

The setting function 45a determines whether the position of a seed point is set by the user. The setting function 45a repeatedly performs determination until it determines that the position of the seed point is set. As described above, the setting function 45a waits until the position of the seed point is set.

Figure 4:
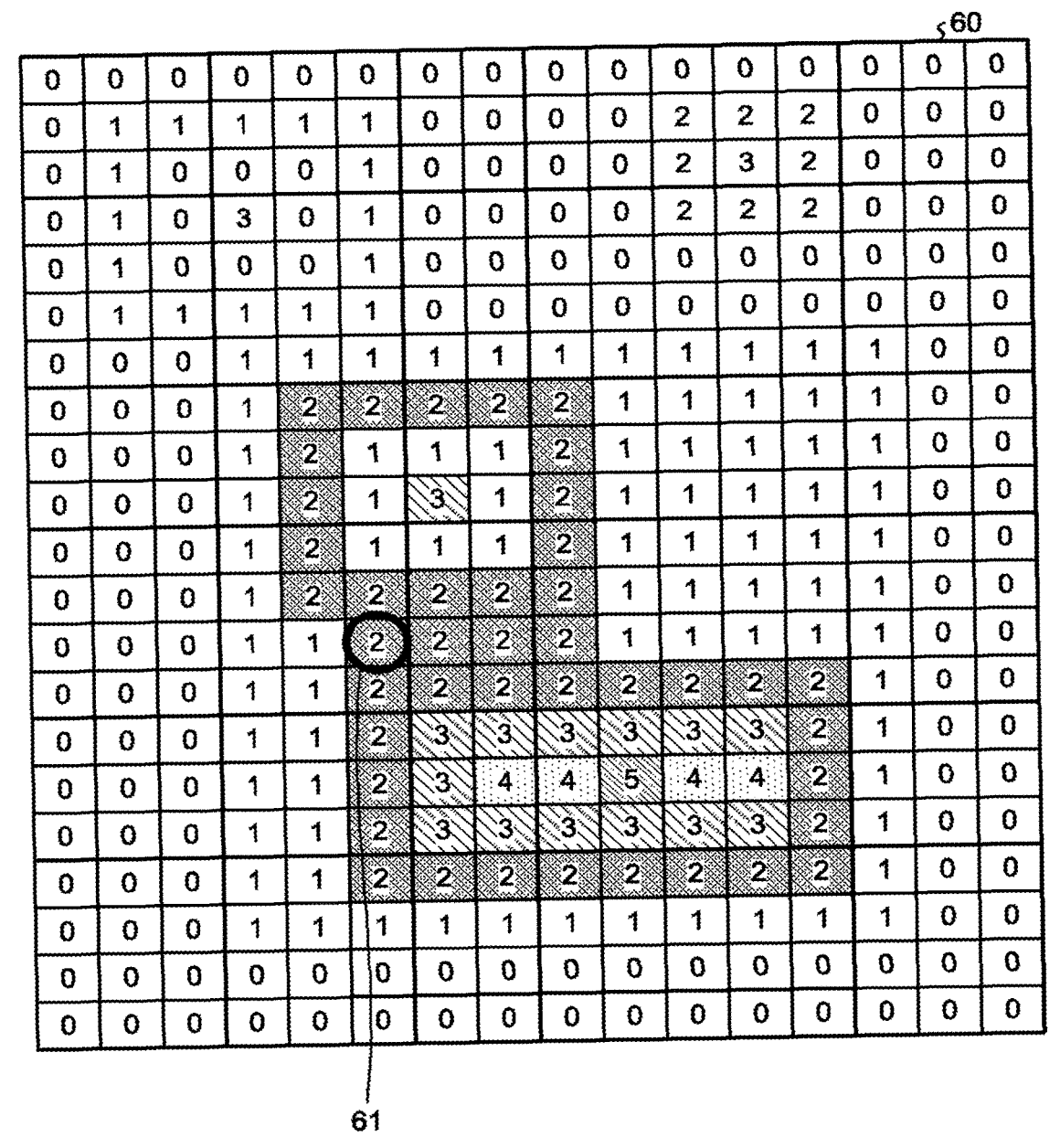

FIG. 4 is a diagram for explaining an example of a method for setting the position of the seed point. As illustrated in FIG. 4, for example, the user may operate the input circuitry 43 to set the position of a pixel 61 as the position of the seed point. Instead of the user's manual operation, the setting function 45a may automatically calculate the position of the seed point with which segmentation is likely to succeed. The setting function 45a, for example, may set the position of the center of the displayed area as the position of the seed point.

The setting function 45a uses the set position of the seed point to perform segmentation with the region growing method. In the segmentation, the setting function 45a sequentially repeats extraction of a pixel that is connected to the seed point and that satisfies the segmentation condition that the luminance of the pixel is equal to or higher than that of a pixel at the set position of the seed point. In other words, the setting function 45a extracts an area that satisfies the segmentation condition based on a comparison between the luminance of the pixel at the position of the seed point in the image indicated by the acquired image data and the segmentation condition. The segmentation is an example of first segmentation and an example of first processing. The segmentation condition is an example of first segmentation condition.

FIG. 5 is a diagram of an example of a segmentation result. Let us assume a case where the position of the pixel 61 is set as the position of the seed point as illustrated in FIG. 4, for example. In this case, the setting function 45a sequentially repeats extraction of a pixel that is connected to the pixel 61 and the luminance of which is "2" or higher, thereby extracting a specific area (hatched area) as illustrated in the example in FIG. 5.

The setting function 45a sets a start point S in the extracted specific area. As illustrated in FIG. 5, for example, the setting function 45a sets a pixel 62 having the highest luminance "5" out of the pixels in the extracted specific area as the start point S. In case where a plurality of pixels have the highest luminance, the setting function 45a, for example, sets a pixel positioned closest to the set position of the seed point out of the pixels having the highest luminance as the start point S. Alternatively, the setting function 45a may set any one of pixels in the largest area of the areas composed of the pixels having the highest luminance as the start point S. Still alternatively, the setting function 45a may set a pixel selected by the user from the pixels having the highest luminance as the start point S. The start point S is also referred to as a reference point because it is a point used as a reference in the processing described later. Setting a reference point is synonymous with setting a reference position corresponding to the position of the reference point.

As described above, the setting function 45a performs segmentation for extracting an area that satisfies the segmentation condition from an image obtained by radiography performed on the subject and sets the reference position in the extracted area. In other words, the setting function 45a performs segmentation on image data indicating the image obtained by radiography performed on the subject to extract an area and sets the reference position in the extracted area. The setting function 45a sets an area having the highest luminance as the reference position out of areas extracted by the segmentation. In other words, the setting function 45a performs segmentation for extracting an area that satisfies the segmentation condition based on a comparison between the pixel value in the image obtained by radiography performed on the subject and the segmentation condition. The setting function 45a sets the reference position in the extracted area.

The generating function 45b changes a variable i from 5 to 0 in stages. The generating function 45b uses the start point S as the seed point to perform segmentation using the region growing method of sequentially repeating extraction of a pixel that is connected to the seed point and that satisfies a segmentation condition C(i) that the luminance of the pixel is equal to or higher than i for the variable i varying from 5 to 0. The area extracted by the segmentation is a connected area including the reference position. D(S, C(i)) denotes an area extracted by segmentation performed under the segmentation condition C(i) using the start point S as the seed point. When i_u and i_l are the upper limit and the lower limit, respectively, to which the variable i is changed, no area corresponding to D(S, C(s)) (s is a value larger than i_u) is present, and an area corresponding to D(S, C(t)) (t is a value equal to or smaller than i_l) is the entire area on the image. The generating function 45b is an example of a generating unit. The upper limit i_u of the variable i in the segmentation condition C(i) according to the present embodiment is set to a value smaller than the minimum value of the variable s in a case where D(S, C(s)) is not present (no corresponding area is present). The lower limit i_l of the variable i in the segmentation condition C(i) is set to a value equal to or larger than the maximum value of the variable t in a case where D(S, C(t)) is the entire area of the image. The segmentation condition C(i) is an example of a second segmentation condition and an example of a processing condition.

The generating function 45b changes the variable i from 5 to 0 in stages and calculates a differential area between an area D(S, C(i+d)) and the area D(S, C(i)) for the variable i varying from 5 to 0. The area D(S, C(i+d)) is extracted by segmentation performed under a segmentation condition C(i+d), and the area D(S, C(i)) is extracted by segmentation performed under the segmentation condition C(i). The generating function 45b updates the luminance in a corrected image, which will be described later, based on the calculated differential area. The generating function 45b, for example, calculates a differential area Ddif(C(i+d), C(i)) between the area D(S, C(i+d)) and the area D(S, C(i)) using Expression (2):

$$D\text{dif}(C(i+d), C(i)) = D(S, C(i)) - D(S, C(i+d)) \qquad (2)$$

The generating function 45b updates the luminance of pixels in the corrected image, which will be described later, corresponding to the pixels constituting the differential area Ddif(C(i+d), C(i)) with i for the variable i varying from 5 to 0. In the present specification, d may be any desired value, and the following describes a case where d is 1. As d decreases, the luminance of the corrected image can be set in a smaller unit; whereas, as d increases, the processing time decreases. The user can set d to a desired value.

The generating function 45b performs the various types of processing described above while reducing the variable i from the maximum value in the range of possible values for the variable i in stages. This is because the generating function 45b can perform processing more simply than a case where it performs the same processing as the various types of processing described above while randomly changing the variable i from the median in the range of possible values for the variable i.

FIG. 6A is a diagram of an example of an initial state of the corrected image. The initial state means a state where the generating function 45b sets no luminance for pixels. As illustrated in FIG. 6A, a corrected image 80 is composed of the same number of pixels as that of the image 60. The pixels of the corrected image 80 correspond to the respective pixels of the image 60. The pixels of the corrected image 80 have certain initial values as the luminance. The pixels of the corrected image may have the same luminance as that of the pixels of the image 60 corresponding thereto.

In a case where the image data indicating the image 60 is three-dimensional data (volume data), the image data indicating the corrected image 80 is three-dimensional data. In a case where the image data indicating the image 60 is two-dimensional data, the image data indicating the corrected image 80 is two-dimensional data.

The generating function 45b performs segmentation under a segmentation condition C(6), thereby extracting an area D(S, C(6)) used to calculate a differential area Ddif(C(6), C(5)), which will be described later. FIG. 6B is a diagram of an example of a result of segmentation performed under the segmentation condition C(6). FIG. 6B illustrates an example of a result of segmentation performed on the image 60 illustrated in the example in FIG. 2. As illustrated in the example in FIG. 5B, the pixels of the image 60 have luminance of 0 to 5 and do not have luminance of 6 or higher. As a result, as illustrated in the example in FIG. 6B, there is no area D(S, C(6)) extracted by the segmentation performed under the segmentation condition C(6).

The following describes a case where the generating function 45b performs segmentation under a segmentation condition C(5), thereby extracting an area D(S, C(5)). FIG. 7A is a diagram of an example of the area D(S, C(5)). FIG. 7B is a diagram of an example of the corrected image in which the luminance of a pixel is updated.

As illustrated in the example in FIG. 7A, the generating function 45b extracts the pixel 62 as the area D(S, C(5)). While the differential area Ddif(C(6), C(5)) is derived by subtracting the area D(S, C(6)) from the area D(S, C(5)), the area D(S, C(6)) is not present as described above. As a result, the generating function 45b determines that the differential area Ddif(C(6), C(5)) is identical with the area D(S, C(5)). As illustrated in the example in FIG. 7B, the generating function 45b updates the luminance of a pixel 81 of the corrected image 80 corresponding to the pixel 62 constituting the differential area Ddif(C(6), C(5)) with "5".

The following describes a case where the generating function 45b performs segmentation under a segmentation condition C(4), thereby extracting an area D(S, C(4)). FIG. 8A is a diagram of an example of the area D(S, C(4)). FIG. 4B is a diagram of an example of the corrected image in which the luminance of pixels is updated.

As illustrated in the example in FIG. 8A, the generating function 45b extracts one pixel 62 and four pixels 63 as the area D(S, C(4)). As illustrated in the example in FIG. the generating function 45b updates the luminance of four pixels 82 of the corrected image 80 corresponding to the four pixels 63 constituting the differential area Ddif(C(5), C(4)) with "4".

The following describes a case where the generating function 45b performs segmentation under a segmentation condition C(3), thereby extracting an area D(S, C(3)). FIG. 9A is a diagram of an example of the area D(S, C(3)). FIG. 9B is a diagram of an example of the corrected image in which the luminance of pixels is updated.

As illustrated in the example in FIG. 9A, the generating function 45b extracts one pixel 62, four pixels 63, and 13 pixels 64 (pixels having luminance of "3" and adjacent to the pixel 62 or the pixels 63) as the area D(S, C(3)). As illustrated in the example in FIG. 9B, the generating function 45b updates the luminance of 13 pixels 83 of the corrected image 80 corresponding to the 13 pixels 64 constituting the differential area Ddif(C(4), C(3)) with "3". While pixels 64a and 64b illustrated in FIG. 9A have luminance of "3", they are not connected to the seed point in the segmentation using the region growing method. Consequently, the luminance of pixels corresponding thereto in the corrected image 80 is not updated.

The following describes a case where the generating function 45b performs segmentation under a segmentation condition C(2), thereby extracting an area D(S, C(2)). FIG. 10A is a diagram of an example of the area D(S, C(2)) FIG. 10B is a diagram of an example of the corrected image in which the luminance of pixels is updated.

As illustrated in the example in FIG. 10A, the generating function 45b extracts one pixel 62, four pixels 63, 13 pixels 64, and 42 pixels 65 (hatched pixels having luminance of "2") as the area D(S, C(2)). As illustrated in the example in FIG. 10B, the generating function 45b updates the luminance of 42 pixels 84 of the corrected image 80 corresponding to the 42 pixels 65 constituting the differential area Ddif(C(3), C(2)) with "2".

Figures 11A, 11B:
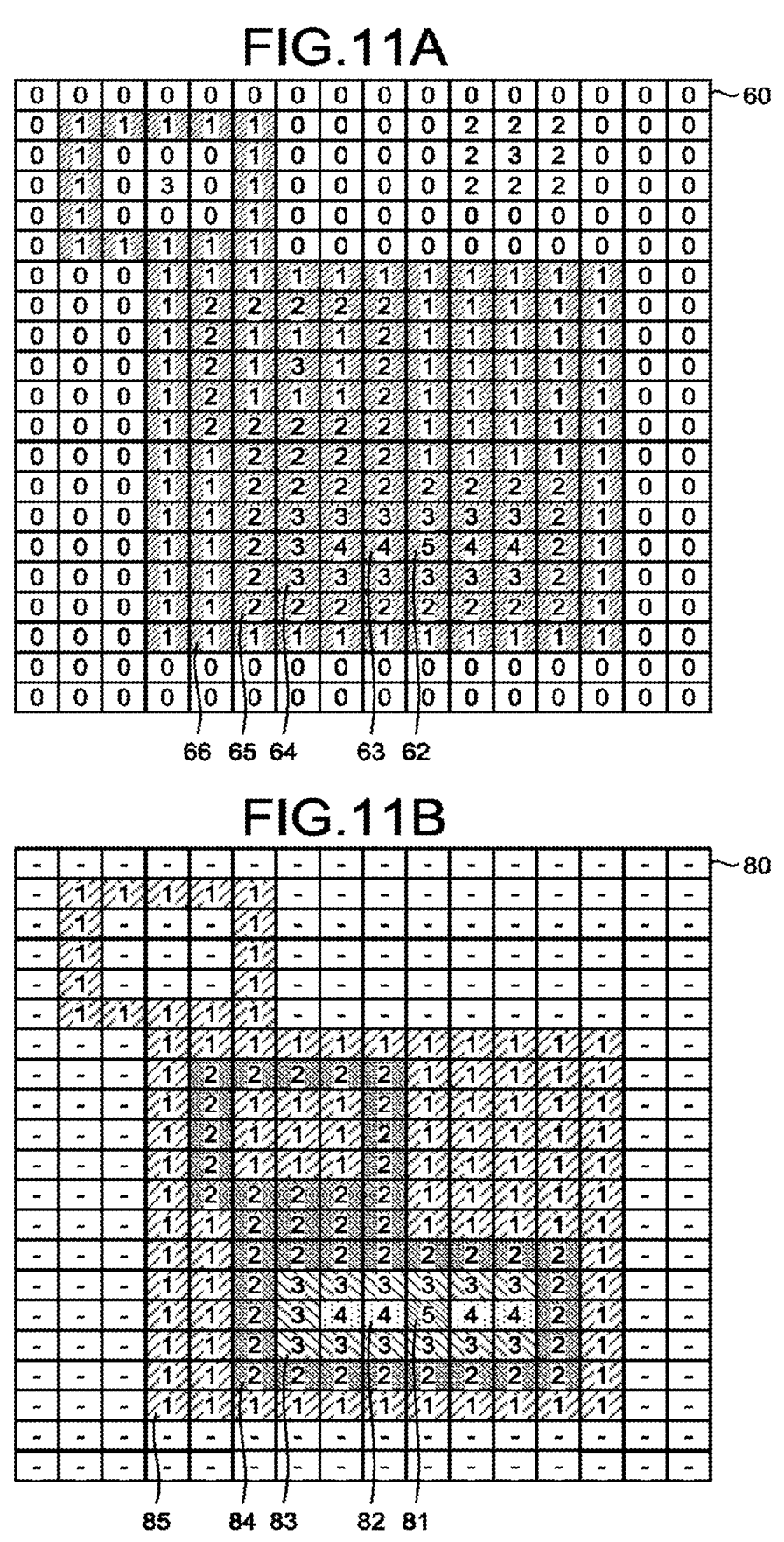

The following describes a case where the generating function 45b performs segmentation under a segmentation condition C(1), thereby extracting an area D(S, C(1)). FIG. 11A is a diagram of an example of the area D(S, C(1)). FIG. 11B is a diagram of an example of the corrected image in which the luminance of pixels is updated.

As illustrated in the example in FIG. 11A, the generating function 45b extracts one pixel 62, four pixels 63, 13 pixels 64, 42 pixels 65, and 98 pixels 66 (hatched pixels having luminance of "1") as the area D(S, C(1)). As illustrated in the example in FIG. 11B, the generating function 45b updates the luminance of 98 pixels 85 of the corrected image 80 corresponding to the 98 pixels 66 constituting the differential area Ddif(C(2), C(1)) with "1".

The following describes a case where the generating function 45b performs segmentation under a segmentation condition C(0), thereby extracting an area D(S, C(0)). FIG. 12A is a diagram of an example of the area D(S, C(0)). FIG. 12B is a diagram of an example of the corrected image in which the luminance of pixels is updated.

As illustrated in the example in FIG. 2A, the generating function 45b extracts one pixel 62, four pixels 63, 13 pixels 64, 42 pixels 65, 98 pixels 66, and all the rest pixels 67 as the area D(S, C(0)). As illustrated in the example in FIG. 12B, the generating function 45b updates the luminance of pixels 86 of the corrected image 80 corresponding to all the rest pixels 67 constituting the differential area Ddif(C(1), C(0)) with "0". Because input of the pixel values for all the pixels of the corrected image 80 is completed, the generating function 45b ends the corrected image generation for generating one corrected image.

The image processing apparatus 40 according to the present embodiment performs the processing described above, thereby generating the corrected image 80 illustrated in FIG. 12B from the image 60 illustrated in FIG. 2. The generating function 45b stores the generated corrected image 80 in the storage circuitry 42. The corrected image 80 is thus saved. The generating function 45b may transmit the generated corrected image 80 to the image storage device 20 and store it in the image storage device 20.

The corrected image 80 is an example of a second image. The image data indicating the corrected image 80 is an example of second image data. The segmentation performed under the segmentation condition C(0) to the segmentation condition C(6) is an example of second segmentation and an example of second processing.

As described above, the generating function 45b uses the point at the reference position set by the setting function 45a as the seed point. The generating function 45b changes the segmentation condition in stages and performs segmentation for extracting an area that satisfies the segmentation condition from the image 60 in stages. The generating function 45b thus generates the corrected image 80 indicating the result of segmentation at each stage and saves the generated corrected image 80. Specifically, the generating function 45b sets the segmentation condition based on the pixel value at the reference position set by the setting function 45a. The generating function 45b changes the set segmentation condition in stages and performs segmentation for extracting an area that satisfies the segmentation condition from the image 60 in stages. The generating function 45b thus generates the corrected image 80 indicating the result of segmentation at each stage and saves the generated corrected image 80. As described above, the generating function 45b sets the segmentation condition based on the pixel value at the reference position set by the setting function 45a. The generating function 45b changes a threshold included in the set segmentation condition in stages and performs segmentation for extracting an area corresponding to the threshold on the image data indicating the image 60 at each stage. The generating function 45b thus generates image data indicating the corrected image 80 including the result of segmentation at each stage and saves the generated image data.

Instead of the generating function 45b, the setting function 45a may set the segmentation condition based on the pixel value at the reference position.

Let us assume a case where the variable i is the threshold. The generating function 45b uses the point at the reference position as the seed point. The generating function 45b reduces the threshold in stages and performs segmentation for extracting a pixel having luminance of equal to or higher than the threshold from the image 60 in stages. The generating function 45b allocates the threshold at each stage to the pixel newly extracted by the segmentation at the stage, thereby generating the corrected image 80. While the threshold is the lower limit of the window in the description above, it is not limited thereto. The threshold may be the lower limit of the window +α (e.g., "50" or "1"), for example.

The following describes corrected image display control for displaying one generated corrected image on the display 44 and/or the terminal device 30.

When the user operates the input circuitry 43 to give a display instruction, to the display control function 45c, to display the corrected image 80 on the display 44 and/or the terminal device 30, the display control function 45c acquires the corrected image 80 from the storage circuitry 42. The display control function 45c displays the acquired corrected image 80 on the display 44 under the display conditions set in advance, such as the window width and the window level. If the lower limit of the window set in advance is "3", for example, the display control function 45c displays pixels having luminance of "4" or higher out of all the pixels of the corrected image 80 illustrated in the example in FIG. 12B on the display 44.

When the user changes the display conditions, the display control function 45c displays the corrected image 80 on the display 44 under the changed display conditions. If the lower limit of the window is changed from "3" to "1", for example, the display control function 45c displays pixels having luminance of "2" or higher out of all the pixels of the corrected image 80 illustrated in the example in FIG. 12B on the display 44.

Even when the display conditions are changed, the present embodiment can display the segmentation result conforming to the changed display conditions without performing the segmentation again. As a result, the present embodiment can quickly display the segmentation result. Furthermore, the present embodiment can suppress reduction in the free space in the storage circuitry 42 because the storage circuitry 42 stores therein only one corrected image 80 that requires less storage capacity. Consequently, the image processing apparatus 40 according to the present embodiment can quickly display the segmentation result using one corrected image 80 serving as information that requires less storage capacity.

Figure 13:
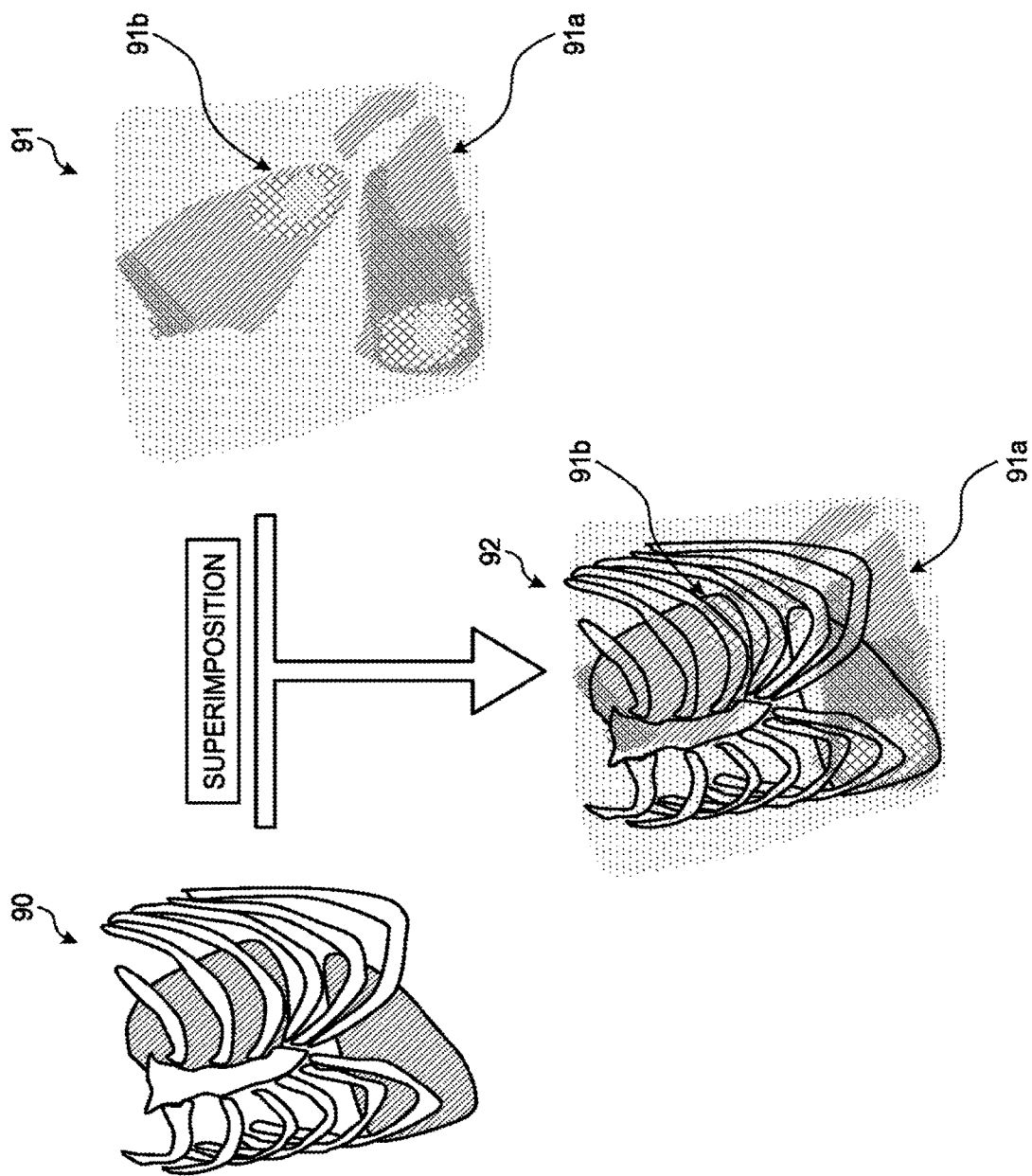
FIG. 13 is a diagram for explaining an example of a case where a CT image and a PET image are simply superimposed and displayed.

The processing described above is useful for superimposing and displaying a plurality of images. The following describes a case where a CT image and a positron emission tomography (PET) image are simply superimposed and displayed, for example. FIG. 13 is a diagram for explaining an example of a case where a CT image and a PET image are simply superimposed and displayed. As illustrated in the example in FIG. 13, the image processing apparatus performs superimposition for superimposing a CT image 90 on a PET image 91 to generate an image 92 in which the CT image 90 is superimposed on the PET image 91 and displays the image 92 on the display. If the user desires to observe a standardized uptake value (SUV) of an area 91a of the liver in the image 92, the distribution of the SUV in areas of regions other than the area 91a of the liver, such as an area 91b of the heart, serves as an obstacle to observation.

Figure 14:
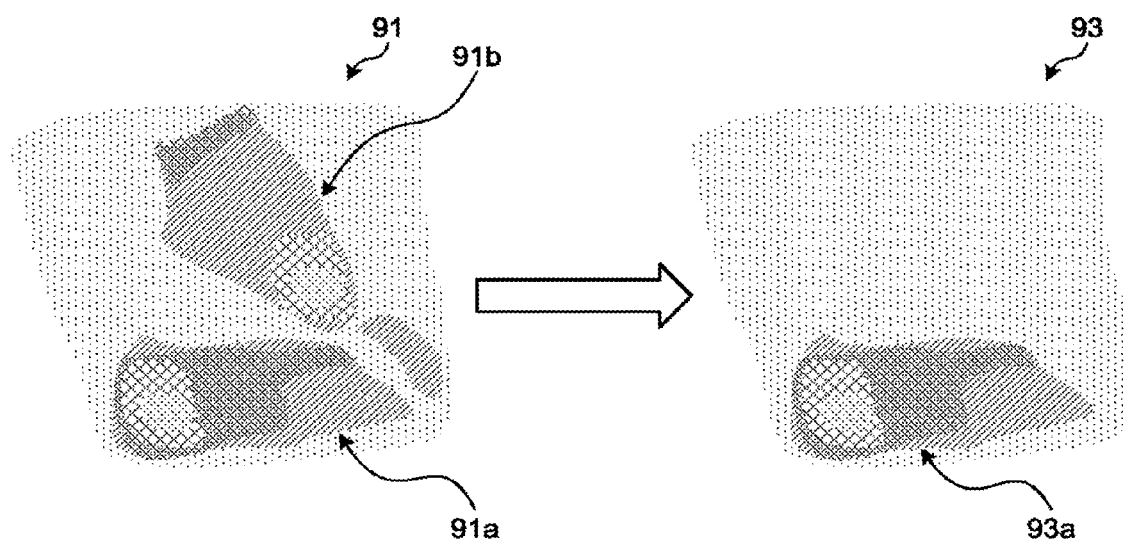
FIG. 14 is a diagram for explaining an example of processing performed by a display control function according to the first embodiment.
Figure 15:
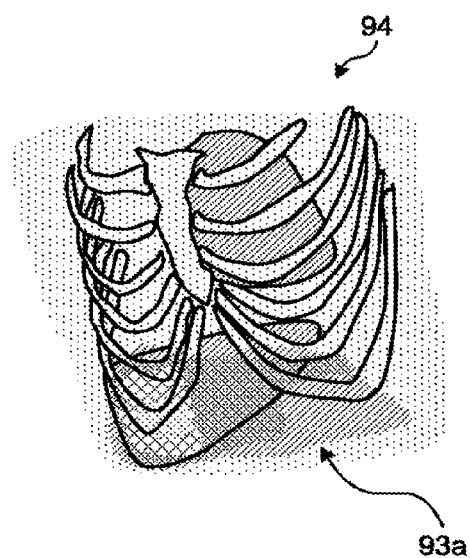
FIG. 15 is another diagram for explaining an example of processing performed by the display control function according to the first embodiment.

FIGS. 14 and 15 are diagrams for explaining an example of processing performed by the display control function according to the first embodiment. When the user sets The position of the seed point in the area 91a of the liver in the displayed PET image 91 as illustrated in the example in FIG. 14, the display control function 45c according to the present embodiment performs the same processing as the processing described above. The display control function 45c thus generates a corrected image 93 by extracting an area 93a of the liver from the PET image 91. The display control function 45c performs superimposition for superimposing the corrected image 93 on the CT image 90 to generate an image 94 in which the corrected image 93 is superimposed on the CT image 90 as illustrated in the example in FIG. 15 and displays the image 94 on the display 44. As a result, the present embodiment can display the SUV of the area 93a of the liver desired to be observed by the user while suppressing the effect of distribution of the SUV in areas of regions other than the area 93a of the liver as illustrated in the example in FIG. 15. Even when the display conditions are changed, the display control function 45c can display the SUV of the area of the liver desired to be observed by the user while suppressing the effect of distribution of the SUV in areas of regions other than the area of the liver based on the changed display conditions.

Figure 16:
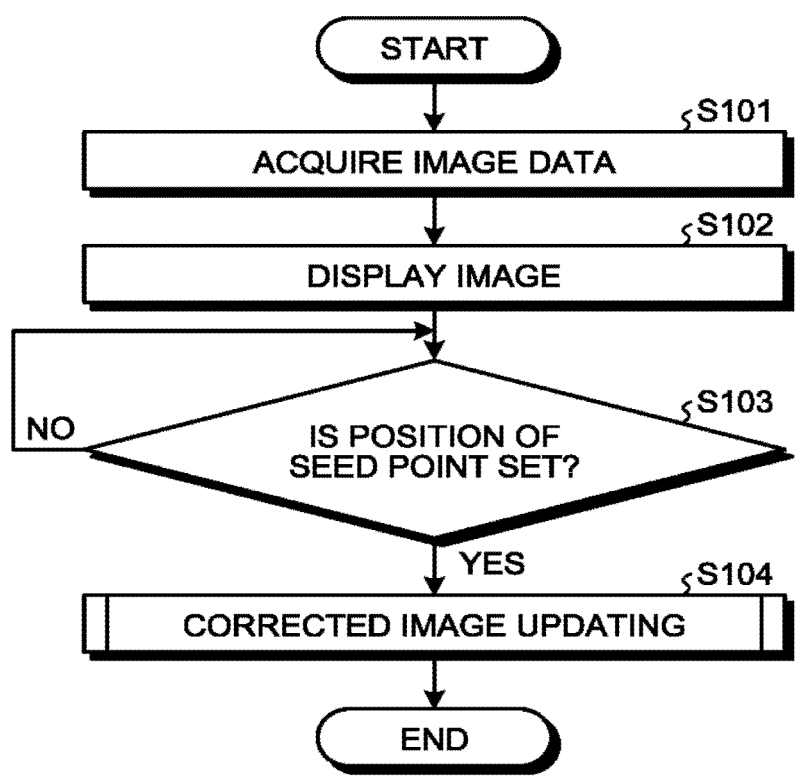
FIG. 16 is a flowchart of an example of the procedure of corrected image generation performed by the image processing apparatus according to the first embodiment.

The following describes an example of the procedure of corrected image generation performed by the image processing apparatus 40 according to the first embodiment. FIG. 16 is a flowchart of an example of the procedure of corrected image generation performed by the image processing apparatus 40 according to the first embodiment. The corrected image generation is performed when the user operates the input circuitry 43 to input an instruction to perform the corrected image generation to the image processing apparatus 40.

As illustrated in the example in FIG. 16, the setting function 45a acquires image data from the image storage device 20 (Step S101). The setting function 45a displays the image 60 on the display 44 and/or the terminal device 30 based on the window width and the window level set in advance (Step S102). At Step S102, the user may change the window width and the window level.

The setting function 45a determines whether the position of the seed point is set by the user (Step S103). If the setting function 45a determines that the position of the seed point is not set (No at Step S103), the setting function 45a performs the determination at Step S103 again. By contrast, if the setting function 45a determines that the position of the seed point is set (Yes at Step S103), the generating function 45b performs corrected image updating (Step S104) and ends the corrected image generation.

Figure 17:
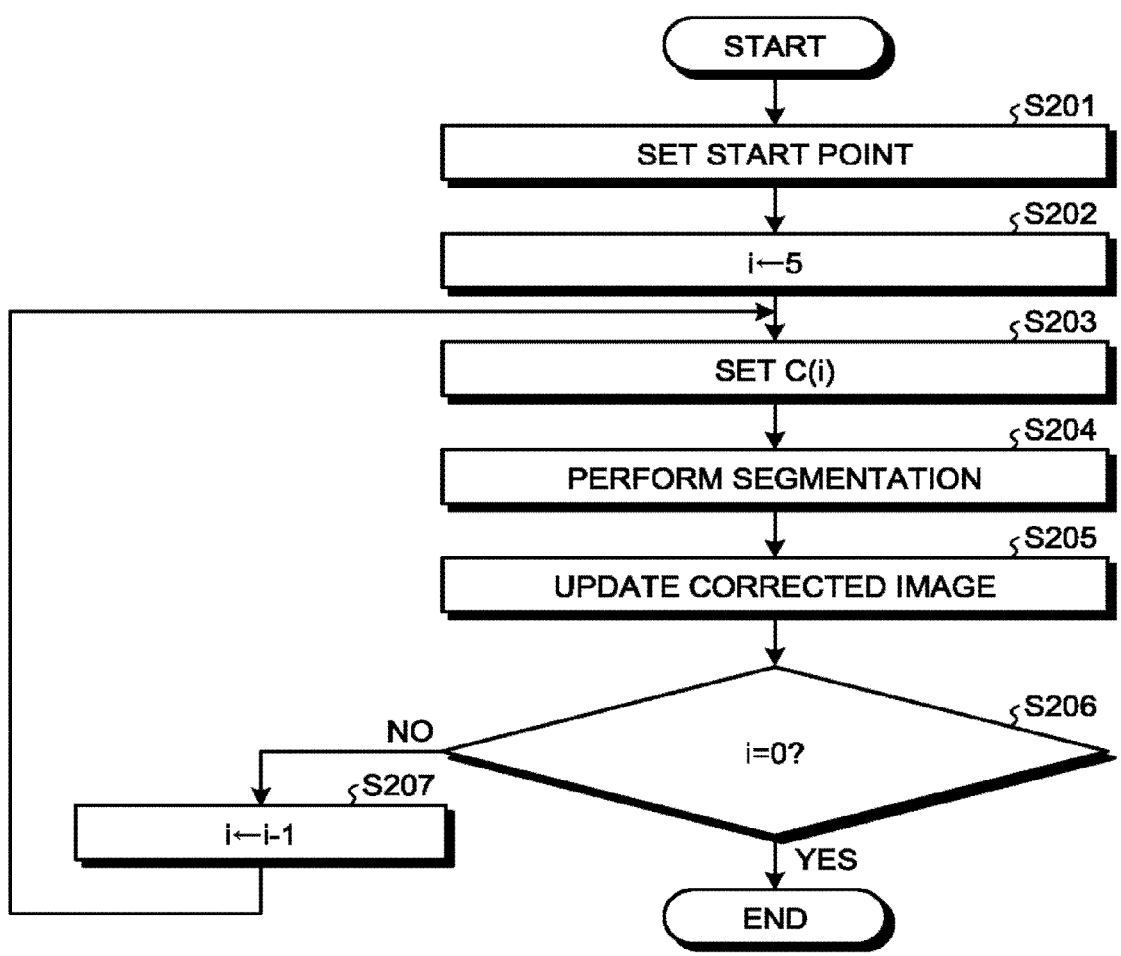
FIG. 17 is a flowchart of an example of the procedure of corrected image updating performed at Step S104.

FIG. 17 is a flowchart of an example of the procedure of corrected image updating performed at Step S104. As illustrated in the example in FIG. 17, the setting function 45a sets the start point S in an extracted specific area (Step S201).

The generating function 45b sets time upper limit i_u for the variable i (Step S202). The generating function 45b sets the luminance of the pixel corresponding to the start point S to "5", for example. The generating function 45*b* sets the segmentation condition C(i) (Step S203).

The generating function 45*b* uses the start point S as the seed point to perform segmentation using the region growing method of sequentially repeating extraction of a pixel that is connected to the seed point and that satisfies the segmentation condition C(i), thereby extracting the area D(S, C(i)) (Step S204).

The generating function 45*b* calculates the differential area Ddif(C(i+d), (Step S204). The generating function 45*b* updates the luminance of pixels of the corrected image 80 corresponding to the pixels constituting the differential area Ddif(C(i+d), C(i)) with "i" (Step S205).

The generating function 45*b* determines whether i is the lower limit i_(e.g., 0) of the variable i, thereby determining whether to end the corrected image updating (Step S206). If the generating function 45*b* determines that i is not 0 (No at Step S206), the generating function 45*b* decrements i by the variable d, that is, decrements i by 1 (Step S207) and performs the processing at Step S203 again. If the generating function 45*b* determines that i is 0 (Yes at Step S206), the generating function 45*b* ends the corrected image updating.

Figure 18:
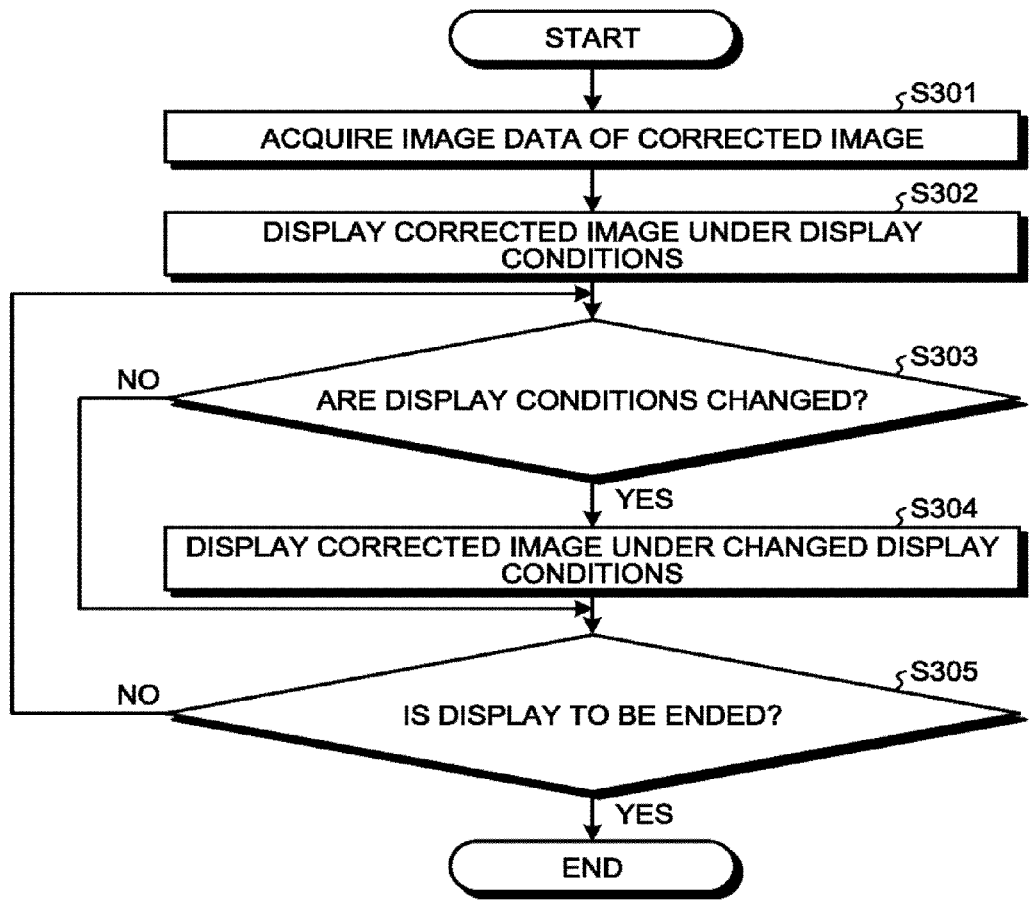
FIG. 18 is a flowchart of an example of the procedure of corrected image display control performed by the image processing apparatus according to the first embodiment.

The following describes an example of the procedure of corrected image display control performed by the image processing apparatus 40 according to the first embodiment. FIG. 18 is a flowchart of an example of the procedure of corrected image display control performed by the image processing apparatus 40 according to the first embodiment. The corrected image display control is performed when the user operates the input circuitry 43 to input a display instruction to perform the corrected image display control to the image processing apparatus 40.

As illustrated in FIG. 18, the display control function 45*c* acquires image data indicating the corrected image 80 from the storage circuitry 42 (Step S301). The display control function 45*c* displays the corrected image 80 on the display 44 under the display conditions set in advance, such as the window width and the window level (Step S302).

The display control function 45*c* determines whether the display conditions are changed by the user (Step S303). If the display control function 45*c* determines that the display conditions are not changed (No at Step S303), the display control function 45*c* performs the processing at Step S305. By contrast, if the display control function 45*c* determines that the display conditions are changed (Yes at Step S303), the display control function 45*c* displays the corrected image 80 on the display 44 under the changed display conditions (Step S304).

The display control function 45*c* determines whether the user operates the input circuitry 43 and inputs an instruction to end display of the corrected image 80 (Step S305). If the display control function 45*c* determines that an instruction to end display is not received (No at Step S305), the display control function 45*c* performs the processing at Step S303 again. By contrast, if the display control function 45*c* determines that an instruction to end display is received (Yes at Step S305), the display control function 45*c* ends the corrected image display control.

The explanation has been made of the image processing apparatus 40 according to the first embodiment. As described above, the image processing apparatus 40 according to the first embodiment can quickly display the segmentation result using one corrected image 80 serving as information that requires less storage capacity even when the display conditions are changed.

First Modification According to the First Embodiment

The display control function 45*c* according to the first embodiment displays the corrected image 80 on the display 44 under the display conditions. Alternatively, the display control function 45*c* may perform another type of display control using the corrected image 80. The following describes an embodiment that performs another type of display control as a first modification according to the first embodiment.

The display control function 45*c* according to the first modification specifies, as a display area, an area composed of pixels the luminance of which is higher than the set lower limit of the window out of all the pixels constituting the corrected image 80. The display control function 45*c* identifies an area in the image 60 corresponding to the specified display area. The display control function 45*c* displays the identified area in the image 60 on the display 44 and/or the terminal device 30. This operation enables the user to observe how the image 60 serving as an original image is displayed depending on the display conditions.

Second Modification According to the First Embodiment

Figure 19:
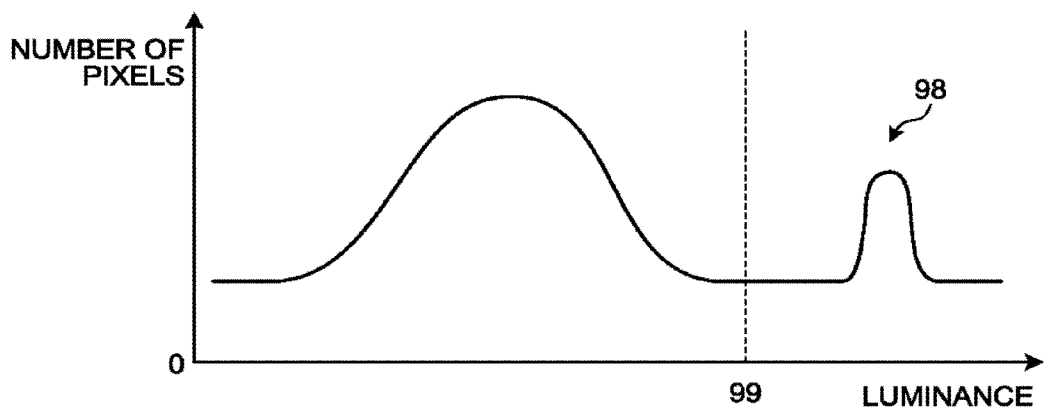
FIG. 19 is a diagram for explaining a second modification according to the first embodiment.

The generating function 45*b* according to the first embodiment changes the variable i within a range from 6 to 0 in stages and performs various types of processing in the corrected image generation. Alternatively, the generating function 45*b* may change the variable i within a desired range in stages and perform various types of processing. FIG. 19 is a diagram for explaining a second modification according to the first embodiment.

In the graph illustrated in FIG. 19, the horizontal axis indicates the luminance of pixels constituting the image 60, and the vertical axis indicates the number of pixels having the luminance indicated by the horizontal axis. In the example illustrated in FIG. 19, reference numeral 98 indicates the number of pixels in an image obtained by radiography performed on a region having high luminance, such as a bone. In the example illustrated in FIG. 19, a threshold 99 indicates the luminance lower than the luminance of pixels in the image obtained by radiography performed on the region, such as a bone. In this case, the generating function 45*b* according to the second modification may reduce the variable i from the luminance corresponding to the threshold 99 in stages, for example, and perform various types of processing. As a result, all the pixels having luminance of equal to or higher than the luminance corresponding to the threshold 99 in the original image serve as pixels having the luminance corresponding to the threshold 99 in the corrected image. The second modification thus enables the user to observe the area where the region, such as a bone, having a value of equal to or higher than the luminance corresponding to the threshold 99 is displayed. This mechanism is useful especially for the user who desires to observe not a change in the luminance of the region, such as a bone, but only the area where the region, such as a bone, is present or the user who need not observe a change in the luminance value of the region, such as a bone.

The processing circuitry 45 (the setting function 45*a* and the generating function 45*b*) according to the embodiment and the modifications thereof performs segmentation for extracting an area using a threshold on the image data indicating the image 60. Alternatively, the processing circuitry 45 may perform another type of processing for extracting an area using a threshold on the image data indicating the image 60. The processing circuitry 45, for example, may perform processing (what is called threshold processing) for extracting pixels having luminance of equal to or higher than a threshold from the image data indicating the image 60. Furthermore, the processing circuitry 45 may perform processing for extracting an area indicating a blood vessel having a diameter of equal to or larger than a threshold from blood vessels (e.g., blood vessels of the heart) depicted in the image 60.

The processing circuitry 45 (generating function 45*b*) according to the embodiment above changes the threshold in stages and performs segmentation on the image data indicating the image 60 at each stage. Alternatively, the processing circuitry 45 may change the range of the luminance in stages and perform segmentation on the image data indicating the image 60 at each stage. The range of the luminance has two thresholds of the upper limit and the lower limit. In other words, the processing circuitry 45 may change the upper limit and the lower limit (two thresholds) in the range of the luminance in stages and perform segmentation on the image data indicating the image 60 at each stage.

The image processing apparatus and the image processing program according to at least one of the embodiment and the modifications thereof can quickly display the segmentation result using one corrected image 80 that requires less storage capacity even when the display conditions are changed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured to:
   set a reference position in an area extracted by performing first processing on first image data,
   set a processing condition based on a pixel value at the reference position, and
   change a threshold included in the processing condition in stages and perform second processing for extracting an area corresponding to the threshold on the first image data at each stage, thereby generating second image data including a result of the second processing at each stage.

2. The image processing apparatus according to claim 1, wherein
   the second processing is segmentation, and
   the area extracted by the second processing is a connected area including the reference position.

3. The image processing apparatus according to claim 1, wherein the processing circuitry generates one piece of second image data indicating the result of the second processing at each stage.

4. The image processing apparatus according to claim 1, wherein the first image data and the second image data are volume data.

5. The image processing apparatus according to claim 1, wherein the processing circuitry reduces the threshold in stages and performs the second processing for extracting a pixel having luminance of equal to or higher than the threshold from the first image data in stages.

6. The image processing apparatus according to claim 1, wherein the processing circuitry allocates the threshold at each stage to a pixel newly extracted by the second processing at the stage, thereby generating the second image data.

7. The image processing apparatus according to claim 1, wherein the processing circuitry sets an area having highest luminance out of the area extracted by the first processing as the reference position.

8. The image processing apparatus according to claim 1, wherein the processing condition in the second processing based on a display condition.

9. The image processing apparatus according to claim 8, wherein the display condition includes a window level and a window width set as the display condition.

10. An image processing method comprising:
    setting a reference position in an area extracted by performing first processing on first image data;
    setting a processing condition based on a pixel value at the reference position; and
    changing a threshold included in the processing condition in stages and performing second processing for extracting an area corresponding to the threshold on the first image data at each stage, thereby generating second image data including a result of the second processing at each stage.

* * * * *